United States Patent
Schmidt

(10) Patent No.: US 9,378,205 B1
(45) Date of Patent: Jun. 28, 2016

(54) SYSTEM AND METHOD FOR MANAGING AND SHARING PHARMACEUTICAL CLINICAL TRIAL REGULATORY DOCUMENTS

(75) Inventor: Zachariah Schmidt, Rancho Cordova, CA (US)

(73) Assignee: SureClinical Inc., Rancho Cordova, CA (US)

( * ) Notice: Subject to any disclaimer, the term of this patent is extended or adjusted under 35 U.S.C. 154(b) by 206 days.

(21) Appl. No.: 12/820,045

(22) Filed: Jun. 21, 2010

Related U.S. Application Data

(60) Provisional application No. 61/218,873, filed on Jun. 19, 2009.

(51) Int. Cl.
*G06F 17/30* (2006.01)

(52) U.S. Cl.
CPC .... *G06F 17/30011* (2013.01); *G06F 17/30587* (2013.01); *H04N 2201/3226* (2013.01)

(58) Field of Classification Search
CPC .................................................. G06F 17/30011
See application file for complete search history.

(56) References Cited

U.S. PATENT DOCUMENTS

| | | | |
|---|---|---|---|
| 2004/0117215 A1* | 6/2004 | Marchosky | 705/3 |
| 2004/0162831 A1* | 8/2004 | Patterson | 707/100 |
| 2005/0138382 A1* | 6/2005 | Hougaard et al. | 713/176 |
| 2006/0106757 A1* | 5/2006 | Sakai et al. | 707/2 |
| 2006/0265731 A1* | 11/2006 | Matsuda | 725/131 |
| 2007/0136262 A1* | 6/2007 | Dettinger | G06F 17/30587 |
| 2007/0186164 A1* | 8/2007 | Getsch | 715/723 |
| 2007/0204164 A1* | 8/2007 | Cattrone et al. | 713/176 |
| 2007/0255512 A1* | 11/2007 | Delenstarr et al. | 702/35 |
| 2008/0017722 A1* | 1/2008 | Snyder et al. | 235/494 |
| 2008/0133295 A1* | 6/2008 | Cappel et al. | 705/7 |
| 2008/0144936 A1* | 6/2008 | Nishikawa | 382/177 |
| 2008/0174790 A1* | 7/2008 | Noguchi et al. | 358/1.1 |
| 2008/0260287 A1* | 10/2008 | Berryman et al. | 382/284 |
| 2008/0298631 A1* | 12/2008 | Nishida | 382/100 |
| 2009/0001167 A1* | 1/2009 | Usuba | 235/462.16 |
| 2009/0070348 A1* | 3/2009 | Uejo | 707/100 |
| 2010/0042585 A1* | 2/2010 | Adler | G06F 17/30587 717/139 |
| 2010/0114900 A1* | 5/2010 | Anderson | G06F 17/30495 707/741 |

* cited by examiner

*Primary Examiner* — Mohammad S Rostami
(74) *Attorney, Agent, or Firm* — Morgan, Lewis & Bockius LLP

(57) ABSTRACT

A method and a system for managing and sharing pharmaceutical clinical trial regulatory documents are described. A computer-implemented method includes receiving an electronic document. The electronic document includes one or more scanned images of a physical document, and the one or more scanned images include one or more optical machine-readable codes. The method also includes storing in the electronic document at least a subset of document information associated with the one or more optical machine-readable codes as metadata.

12 Claims, 13 Drawing Sheets

Figure 5A

| My Recent Views | Document Navigator | By Study 512-1 | | 18113-10-1110-1572-001.pdf |
|---|---|---|---|---|
| Acquire Scan 1570 | ☐ Study 18113 | | | ◁▷ 2/5 |
| Reports: View all | ☐ Site 10 | | | |
| Manage: Add new user | ☒ 18113-10-1110-1572-001.pdf | | | STATEMENT OF INVESTIGATOR |
| | ☐ 18113-10-1150-Protocol-001.pdf | | | 1. NAME AND ADDRESS OF INVESTIG |
| | ☐ Albright, Lori | | | Lori Albright, 12345 Clinical Way, Fols |
| | ☐ 18113-10-1120-FD-LA-111123-001.pdf | | | 2. EDUCATION, TRAINING, AND EXPE |
| Form Library | Document Metadata Viewer | | | CURRICULUM VITAE |
| | Document Database Form 1572 | | | 3. NAME AND ADDRESS OF ANY MED |
| Downloadable Forms: | Doc Name: 1572   Status: Scanned | | | 4. NAME AND ADDRESS OF ANY CLIN |
| Site Questionnaire | Site: 18113-10   CRA: Allen King | | | 5. NAME AND ADDRESS OF THE IRB |
| Informed Consent | Staff: Albright, Lori   Role: Principal Investigator | | | |
| | Created: 3/27/2008  Modified: 3/27/2008 | | | |
| | Date Signed: 01/20/2008 | | | |

Figure 5B

SYSTEM AND METHOD FOR MANAGING AND SHARING PHARMACEUTICAL CLINICAL TRIAL REGULATORY DOCUMENTS

RELATED APPLICATIONS

This application claims priority to U.S. Provisional Application Ser. No. 61/218,873, filed Jun. 19, 2009, entitled "System for Managing and Sharing Pharmaceutical Clinical Trial Regulatory Documents," which is incorporated herein by reference in its entirety.

TECHNICAL FIELD

This relates generally to document management systems, including but not limited to document management systems for pharmaceutical clinical trial regulatory documents.

BACKGROUND

Pharmaceutical clinical trials (often referred to as "studies" in the pharmaceutical industry) play an important role in drug developments, because clinical trials are used to collect safety and efficacy data of drug candidates (e.g., small molecules, biologics, and combination devices). In some instances, pharmaceutical companies can spend over $100 million to conduct a clinical trial. Safety and efficacy data from clinical trials, and sometimes even communications to and from clinical trial investigators (also called principal investigators) and other documents need to be recorded accurately and maintained pursuant to government regulations in order for the drug candidates to obtain regulatory approval by government agencies.

Many clinical trial documents require signatures, for example, of clinical trial investigators or patients. Hardcopy documents (e.g., documents printed on paper), rather than softcopy documents (e.g., electronic documents), are frequently used in clinical trials for various reasons (e.g., ease to prove authenticity and integrity). However, tracking and maintaining all regulatory documents throughout clinical trials, some of which may last over years, is not an easy task. The cost of losing key clinical trial documents can be significant because it may render data from a multi-year clinical trial useless or in want of an expensive follow-up clinical trial. Therefore, there is a need for a better system and method for managing and sharing pharmaceutical clinical trial regulatory documents.

SUMMARY

A number of embodiments (e.g., of server systems, client systems or devices, and methods of operating such systems or devices) that overcome the limitations and disadvantages described above are presented below. These embodiments provide computer-implemented methods, systems, and graphical user interfaces (GUIs) for managing and sharing clinical trial regulatory documents.

As described in more detail below, some embodiments involve a computer-implemented method performed at a computer system having one or more processors and memory storing one or more programs for execution by the one or more processors to perform the method. The method includes receiving an electronic document that includes one or more scanned images of a physical document. The one or more scanned images include one or more optical machine-readable codes. At least a subset of document information associated with the one or more optical machine-readable codes is stored in the electronic document as metadata.

In accordance with some embodiments, a system includes one or more processors, memory, and one or more programs stored in the memory. The one or more programs are configured for execution by the one or more processors. The one or more programs include instructions for receiving an electronic document that includes one or more scanned images of a physical document. The one or more scanned images include one or more optical machine-readable codes. The one or more programs also include instructions for storing in the electronic document at least a subset of document information associated with the one or more optical machine-readable codes as metadata.

In accordance with some embodiments, a computer readable storage medium stores one or more programs configured for execution by one or more processors of a computer system. The one or more programs include instructions for receiving an electronic document that includes one or more scanned images of a physical document. The one or more scanned images include one or more optical machine-readable codes. The one or more programs also include instructions for storing in the electronic document at least a subset of document information associated with the one or more optical machine-readable codes as metadata.

In accordance with some embodiments, a computer-implemented method is performed at a computer system having one or more processors and memory storing one or more programs for execution by the one or more processors to perform the method. The method includes receiving a first document and document information. The first document is converted into a second document. The second document comprises a first portion for storing document content and a second portion for storing metadata. The first portion includes content of the first document, and the second portion is configured to include metadata. At least a subset of the document information is stored in the second portion of the second document as metadata. The second document that includes at least a subset of the document information is stored.

In accordance with some embodiments, a system includes one or more processors, memory, and one or more programs stored in the memory. The one or more programs are configured for execution by the one or more processors. The one or more programs include instructions for receiving a first document and document information and for converting the first document into a second document. The second document comprises a first portion for storing document content and a second portion for storing metadata. The first portion includes content of the first document, and the second portion is configured to include metadata. The one or more programs also include instructions for storing in the second portion of the second document at least a subset of the document information as metadata. The one or more programs further include instructions for storing the second document that includes at least a subset of the document information.

In accordance with some embodiments, a computer readable storage medium stores one or more programs configured for execution by one or more processors of a computer system. The one or more programs include instructions for receiving a first document and document information and for converting the first document into a second document. The second document comprises a first portion for storing document content and a second portion for storing metadata. The first portion includes content of the first document, and the second portion is configured to include metadata. The one or more programs also include instructions for storing in the second portion of the second document at least a subset of the document information as metadata. The one or more programs further include instructions for storing the second document that includes at least a subset of the document information.

In accordance with some embodiments, a computer-implemented method performed at a server having one or more processors and memory storing one or more programs for execution by the one or more processors to perform the method. The method includes sending to a client system a set of instructions. The set of instructions includes instructions for receiving an electronic document that includes one or more scanned images of a physical document. The one or more scanned images include one or more optical machine-readable codes. The set of instructions includes instructions for storing at least a subset of document information associated with the one or more optical machine-readable codes in the electronic document as metadata.

In accordance with some embodiments, a server system includes one or more processors, memory, and one or more programs stored in the memory. The one or more programs are configured for execution by the one or more processors. The one or more programs include instructions for sending to a client system a set of instructions. The set of instructions includes instructions for receiving an electronic document that includes one or more scanned images of a physical document. The one or more scanned images include one or more optical machine-readable codes. The set of instructions also includes instructions for storing at least a subset of document information associated with the one or more optical machine-readable codes in the electronic document as metadata.

In accordance with some embodiments, a computer readable storage medium stores one or more programs configured for execution by one or more processors of a computer system. The one or more programs include instructions for sending to a client system a set of instructions. The set of instructions includes instructions for receiving an electronic document that includes one or more scanned images of a physical document. The one or more scanned images include one or more optical machine-readable codes. The set of instructions also includes instructions for storing at least a subset of document information associated with the one or more optical machine-readable codes in the electronic document as metadata.

In accordance with some embodiments, a computer-implemented method performed at a computer system having one or more processors and memory storing one or more programs for execution by the one or more processors to perform the method. The method includes receiving an electronic document and document information associated with one or more machine-readable codes. The electronic document includes one or more scanned images of a physical document. The method also includes storing in the electronic document at least a subset of document information associated with the one or more machine-readable codes as metadata.

In accordance with some embodiments, a system includes one or more processors, memory, and one or more programs stored in the memory. The one or more programs are configured for execution by the one or more processors. The one or more programs include instructions for receiving an electronic document and document information associated with one or more machine-readable codes. The electronic document includes one or more scanned images of a physical document. The one or more programs also include instructions for storing in the electronic document at least a subset of document information associated with the one or more machine-readable codes as metadata.

In accordance with some embodiments, a computer readable storage medium stores one or more programs configured for execution by one or more processors of a computer system. The one or more programs include instructions for receiving an electronic document and document information associated with one or more machine-readable codes. The electronic document includes one or more scanned images of a physical document. The one or more programs also include instructions for storing in the electronic document at least a subset of document information associated with the one or more machine-readable codes as metadata.

BRIEF DESCRIPTION OF THE DRAWINGS

For a better understanding of the aforementioned aspects of the invention as well as additional aspects and embodiments thereof, reference should be made to the Description of Embodiments below, in conjunction with the following drawings in which like reference numerals refer to corresponding parts throughout the figures.

FIGS. 5A-5B are exemplary user interfaces of a web application in accordance with some embodiments

DESCRIPTION OF EMBODIMENTS

Methods and systems for managing and sharing clinical trial regulatory documents are described. Reference will be made to certain embodiments of the invention, examples of which are illustrated in the accompanying drawings. While the invention will be described in conjunction with the embodiments, it will be understood that it is not intended to limit the invention to these particular embodiments alone. On the contrary, the invention is intended to cover alternatives, modifications, and equivalents that are within the spirit and scope of the invention as defined by the appended claims.

Moreover, in the following description, numerous details are set forth to provide a thorough understanding of the present invention. However, it will be apparent to one of ordinary skill in the art that the invention may be practiced without these particular details. In other instances, methods, procedures, components, and networks that are well-known to those of ordinary skill in the art are not described in detail to avoid obscuring aspects of the present invention.

It will also be understood that, although the terms first, second, etc. may be used herein to describe various elements, these elements should not be limited by these terms. These terms are used only to distinguish one element from another. For example, a first contact could be termed a second contact and, similarly, a second contact could be termed a first contact without departing from the scope of the present invention. The first contact and the second contact are both contacts, but they are not the same contact.

The terminology used in the description of the embodiments herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on context. Similarly, the phrase "if it is determined" or "if [a stated condition or event] is detected" may be construed to mean "upon determining," "in response to determining," or "upon detecting (the stated condition or event)" or "in response to detecting (the stated condition or event)," depending on the context.

Figure 1:
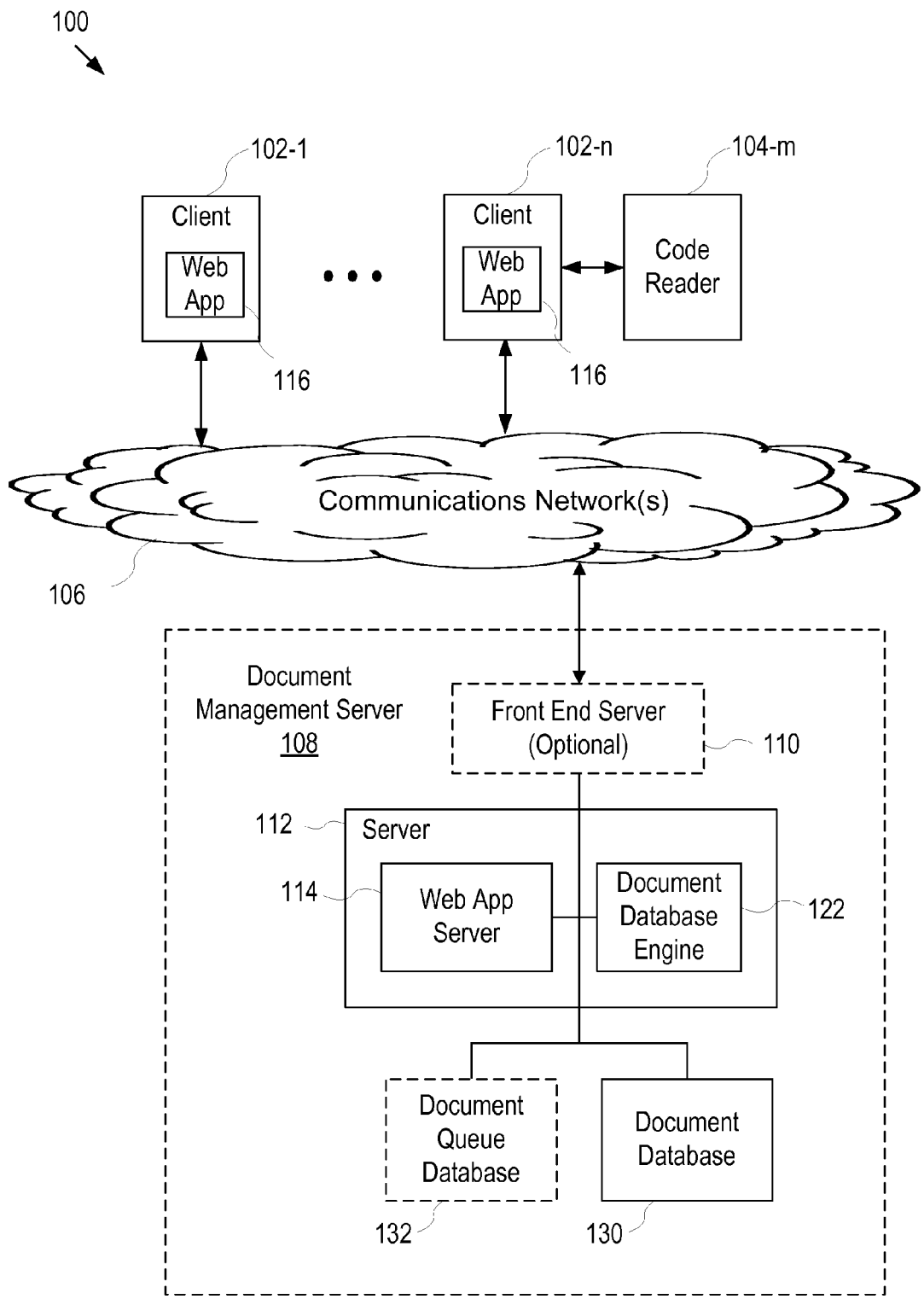
FIG. 1 is a block diagram illustrating an exemplary distributed computer system in accordance with some embodiments.

FIG. 1 is a block diagram illustrating an exemplary distributed computer system 100, according to certain embodiments. The system 100 includes one or more client computers 102, communications network(s) 106, and a document management server 108. Various embodiments of the document management server 108 implement the document management methods described in this document.

The client computers 102 can be any number of different types of computing devices (e.g., Internet kiosks, personal digital assistants, cell phones, gaming devices, desktop computers, laptop computers, tablet computers, handheld computers, or combinations thereof) used to enable the activities described below. Client computer(s) 102 are also referred to herein as client(s). A client 102 includes a user interface (UI) 300 (shown in FIG. 3) that is employed by a user of the client to interact with programs that execute on the client 102. In some embodiments, the UI 300 is a graphical user interface (GUI) 111. Some of the clients 102 are coupled to a code reader 104 (e.g., an optical scanner, a barcode reader, a radio-frequency identification (RFID) reader, etc.) by direct connection (as shown in FIG. 1) or through communication network(s) 106, and receive codes associated with physical documents (e.g., barcodes in scanned images of the physical documents, RFID signal from an RFID tag attached to the physical document, etc.) from respective code readers 104. When the code reader 104 comprises an optical scanner (also called an image scanner herein), the code reader 104 (e.g., the optical scanner) is configured to generate scanned images of a physical document. In some embodiments, the code reader 104 includes both an optical scanner and an RFID reader. Such clients 102 coupled to respective code readers 104 are configured to receive codes associated with physical documents (e.g., scanned images of physical documents including barcodes). Client 102 is connected to the document management server 108 via communications network(s) 106. As described in more detail below, the UI 300 is used to display metadata and scanned images of documents. The document management server 108 provides document management services (e.g., view, edit, and create documents) to users who access the document management server 108 from the clients 102. The clients 102 are described in greater detail below with reference to FIG. 3.

A document management system 108 includes one or more servers, such as a server 112, connected to communications network(s) 106. Optionally, the one or more servers are connected to the communications network 106 via a front end server 110 (e.g., a server that conveys (and optionally parses) inbound requests to the appropriate server of the system 108 and that formats responses and/or other information being sent to clients in response to requests). The front end server 110, if present, may be a web server providing web based access to the document management server 108. The front end server 110, if present, may also be a router server that routes communications to and from other destinations, such as clients.

A document management server 108 includes a document database 130 and optionally, a document queue database 132. The server 112 communicates with databases internal to the document management server 108, such as the document database 130 and the document queue database 132 by internal communication buses, or by any other appropriate mechanism or combination of mechanism. In some embodiments, the server 112 communicates with databases via another server. For example, a document management server 108 may include a separate document database server (not shown), and the server 112 may communicate with document database 130 via the document database server. In some embodiments, one or more databases are located in a remote database server and the document management server 108 has access to the remote database server (e.g., by communication network(s) 106).

The server 112 communicates with clients 102 via the front end server 110 (if present) and communication network(s) 106. In some embodiments, communications network 106 is or includes the Internet. In some embodiments, communication network 106 is or includes a wired or wireless telephone network. In other embodiments, communication network 106 can be any local area network (LAN), wide area network (WAN), metropolitan area network, or a combination of such networks. In some embodiments, the server 112 is a web server that provides document management services using appropriate communication protocols. Alternatively, if the server 112 is used within an intranet or other local area network, it may be an intranet or LAN server.

In some embodiments, the server 112 includes a web application (also called "web app" herein) server 114. The web app server 114 distributes web apps 116 to clients 102, and supports operation of the web apps 116 at clients 102 by processing requests sent by the web apps 116 on clients 102 (e.g., receiving requests from the web apps 116 on clients 102 and sending requested data to clients 102, receiving documents from the web apps 116 on clients 102 and storing the received documents in the document database 130, etc.).

In some embodiments, the server includes a document database engine 122, where the document database engine 122 assists in accessing and updating one or more databases, including the document database 130 and the document queue database 132 (optional).

A document database 130 stores documents and document information. The document database 130 is described in greater detail below with reference to FIG. 4B. In some embodiments, the document database 130 includes one or more databases, such as the document queue database 132.

In some embodiments, the document queue database 132 is configured to store documents and document information before the documents are indexed in the document database 130. Thus, in some embodiments, respective documents and document information stored in the document queue database 132 are deleted when the documents and document information are stored in the document database 130. The document queue database 130 is described in greater detail below with reference to FIG. 4A. In some embodiments, the document queue database 132 is included in the document database 130.

In some embodiments, a respective client 102 includes a respective web app 116. The web app 116 performs one or more of: receiving scanned images of a physical document, converting the scanned images into an electronic document, retrieving document information, storing the document information in the electronic document, and storing the electronic document. The web app 116 is described in greater detail below with reference to FIG. 3.

In some embodiments, fewer and/or additional modules, functions, or databases are included in the document management server 108 and the server 112. The modules shown in the document management server 108 and the server 112 in FIG. 1 represent functions performed in certain embodiments. In some embodiments, the server 112 may include a separate web app distribution server, and the web app server 114 may not distribute web apps directly.

Figure 2:
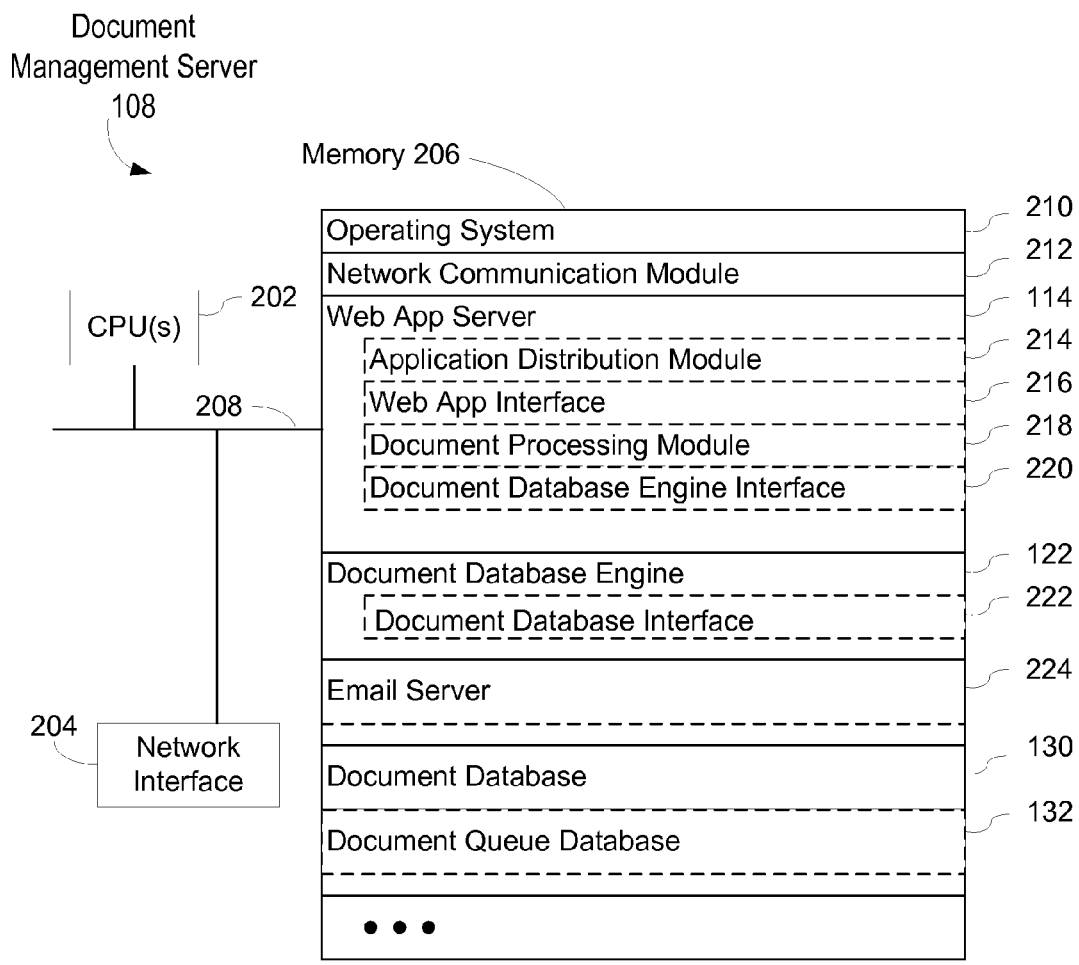
FIG. 2 is a block diagram illustrating a document management server in accordance with some embodiments.

FIG. 2 is a block diagram illustrating the document management server 108 in accordance with some embodiments. The document management server 108 typically includes one or more processing units (CPUs) 202, one or more network or other communications interfaces 204, memory 206, and one or more communication buses 208 for interconnecting these components. In some embodiments, communication buses 208 include circuitry (sometimes called a chipset) that interconnects and controls communications between system components. In some other embodiments, the document management server 108 includes a user interface (not shown) (e.g., a user interface having a display device, a keyboard, and a mouse or other pointing device), but when implemented as a server, the document management server 108 is more typically controlled from and accessed by various client systems (e.g., clients 102).

Memory 206 of the document management server 108 includes high-speed random access memory, such as DRAM, SRAM, DDR RAM, or other random access solid state memory devices, and may include non-volatile memory, such as one or more magnetic disk storage devices, optical disk storage devices, flash memory devices, or other non-volatile solid state storage devices. Memory 206 may optionally include one or more storage devices remotely located from the CPU(s) 202. Memory 206, or alternately the non-volatile memory device(s) within memory 206, comprises a computer readable storage medium. In some embodiments, the computer readable storage medium includes a non-transitory computer readable storage medium. In some embodiments, memory 206 or the computer readable storage medium of memory 206 stores the following programs, modules and data structures, or a subset thereof:

- an Operating System 210 that includes procedures for handling various basic system services and for performing hardware dependent tasks;
- a Network Communication Module (or instructions) 212 that is used for connecting the document management server 108 to other computers (e.g., clients 102) via the one or more network interfaces 204 and one or more communications networks 106 (FIG. 1), such as the Internet, other wide area networks, local area networks, metropolitan area networks, and so on; and
- a Web App Server 114 that is used for supporting web apps executed on clients 102;
- a Document Database Engine 122 that is used for retrieving and updating data from the document database 130 and the (optional) document queue database 132; the document database engine 122 may include a document database interface 222, which is used to transfer data to and from the databases (e.g., the document database 130 and/or the document queue database 132); exemplary document database interfaces include database schema, data dictionary, and lookup tables;
- (optional) an Email Server 224 that is used to send and/or receive electronic documents as attachments of one or more emails;
- a Document Database 130; and
- (optional) a Document Queue Database 132.

In some embodiments, the Web App Server 114 includes the following modules, or a subset or superset thereof:

- an Application Distribution Module 214, which sends one or more programs or a set of instructions to clients 102 such that the one or more programs or the set of instructions can be executed by processors of the client 102 as web applications;
- a Web App Interface 216, which receives requests from web apps located on clients 102, and sends data and/or instructions to the web apps located on clients 102;
- a Document Processing Module 218, which processes the requests from the web apps (e.g., performs a query or updates a database index, etc.); and
- a Document Database Engine Interface, which is used to send and/or receive commands and/or data to and from the document database engine 122.

Each of the above identified modules and applications corresponds to a set of instructions for performing one or more functions described herein. These modules (i.e., sets of instructions) need not be implemented as separate software programs, procedures, or modules, and thus various subsets of these modules may be combined or otherwise rearranged in various embodiments. In some embodiments, memory 206 may store a subset of the modules and data structures identified above. Furthermore, memory 206 may store additional modules and data structures not described above.

Notwithstanding the discrete blocks in FIGS. 1 and 2, these figures are intended to be a functional description of some embodiments rather than a structural description of functional elements in the embodiments. One of ordinary skill in the art will recognize that an actual implementation might have the functional elements grouped or split among various components. In practice, and as recognized by those of ordinary skill in the art, items shown separately could be combined and some items could be separated. For example, in some embodiments, the web app server 114 and the document database engine 122 are parts of a single application. In other embodiments, the document database engine 122 is implemented using one or more servers whose primary function is to store and process document data. In some embodiments, the document database 130 is stored in a remote database server located outside the document management server 108. Similarly, the email server 224 can be implemented on one or more servers within the document management server 108 or in one or more remote servers different from the document management server 108.

The actual number of servers used to implement the document management server 108 and how features are allocated among them will vary from one implementation to another, and may depend in part on the amount of data traffic that the system must handle during peak usage periods as well as during average usage periods, and may also depend on the amount of data stored by the document management server 108. Moreover, one or more of the blocks in FIGS. 1 and 2 may be implemented on one or more servers designed to provide the described functionality. Although the description herein refers to certain features implemented in client 102 and certain features implemented in server 112, the embodiments are not limited to such distinctions. For example, features described herein as being part of server 112 can be implemented in whole or in part in client 102, and vice versa. For example, in some embodiments, the web app 116 and some or all of its associated components can be implemented on the document management server 108.

Figure 3:
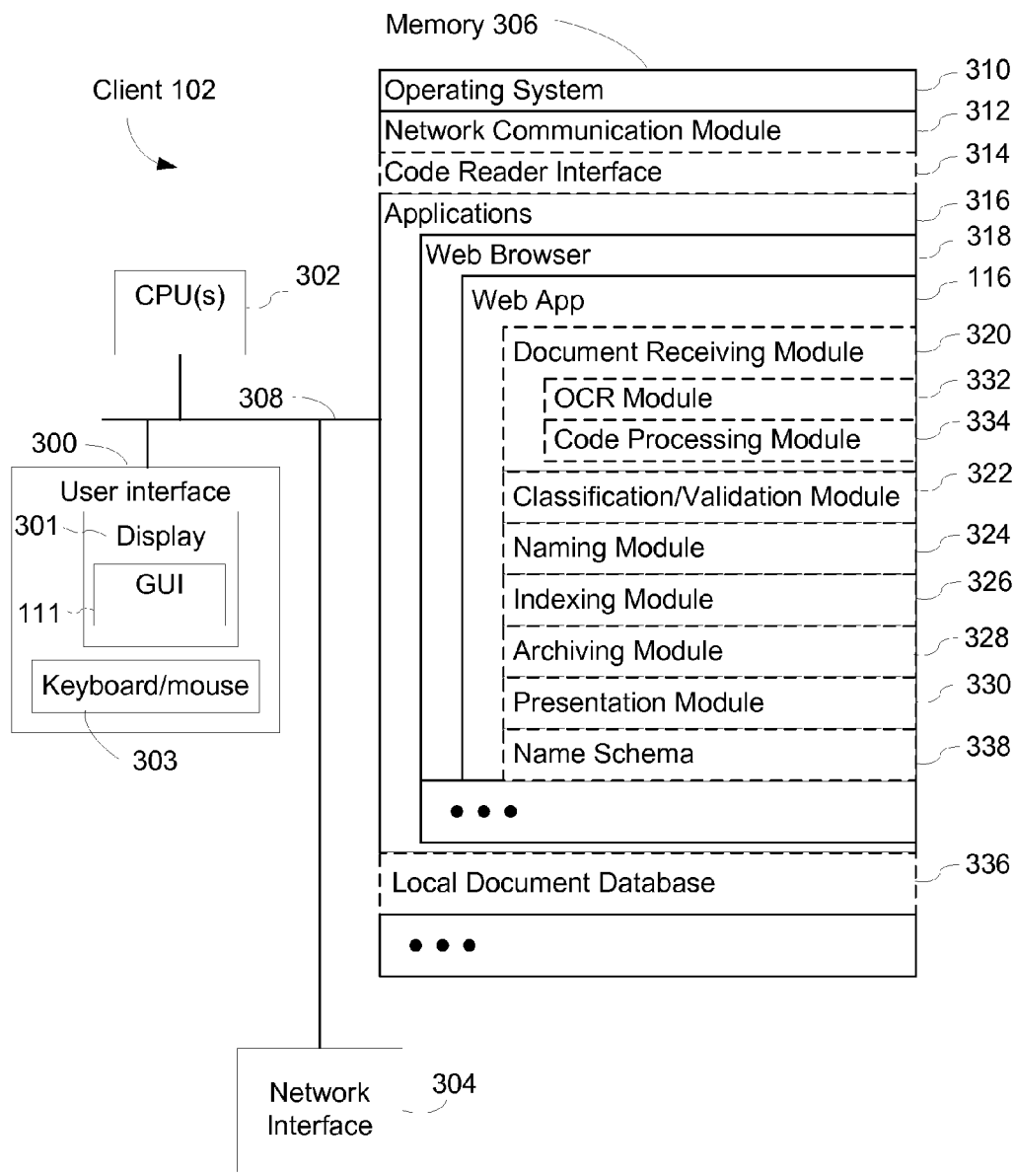
FIG. 3 is a block diagram illustrating a client in accordance with some embodiments.

FIG. 3 is a block diagram illustrating a client, also called client systems or client devices in accordance with some embodiments. Clients 102 as shown in FIGS. 1 and 3 are configured for use by a user of the document management server 108. The client 102 includes a user interface 300, which typically includes a display device 301 and one or more input devices 303, such as a keyboard and a mouse or other pointing device. As noted above, the client 102 includes the graphical user interface (GUI) 111, which is displayed on display device 301. A client 102 typically includes one or more processing units (CPUs) 302, one or more network or other network communications interfaces 304, memory 306, and one or more communication buses 308 for interconnecting these components. Communication buses 308 may include circuitry (sometimes called a chipset) that interconnects and controls communications between system components.

Memory 306 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. Memory 306 may optionally include one or more storage devices remotely located from the CPU(s) 302. Memory 306, or alternately the non-volatile memory device(s) within memory 306, comprises a computer readable storage medium. In some embodiments, the computer readable storage medium includes a non-transitory computer readable storage medium. In some embodiments, memory 306 or the computer readable storage medium of memory 306 stores the following programs, modules, and data structures, or a subset thereof:

- an Operating System 310 that includes procedures for handling various basic system services and for performing hardware dependent tasks;
- a Network Communication Module (or instructions) 312 that is used for connecting client 102 to other systems (e.g., the document management server 108 and other clients 102) via the one or more communications Network Interfaces 304 (wired or wireless) and one or more communication networks 106 (FIG. 1), such as the Internet, other wide area networks, local area networks, metropolitan area networks, telephone networks, and so on;
- a Code Reader Interface 314 (e.g., when the code reader is an optical scanner, the code reader interface 314 may be based on the TWAIN protocol) that is used for operating one or more code readers coupled to the client 102 (e.g., receiving scanned images from the one or more scanners);
- Applications 316 including a web browser 318 that includes a web app 116; and
- (optional) a Local Document Database 336 that stores documents and document information as a cache (e.g., storing documents that are currently and/or frequently used), as a temporary storage (e.g., storing documents before the documents are stored in a different document database (e.g., the document database 130 in the document management server 108)), and/or for persistency (e.g., retain documents for use while the connection between the client 102 and the document management server 108 is impaired) or portability (e.g., enable access to the documents when the client 108 is at a location without a network connection to the document management server 108).

The web app 116 may be based on Active X, Java script, Java applet, Ajax, Comet, or any other programming languages and tools. In some embodiments, the web app 116 includes one or more of the following modules, or a subset or superset thereof:

- a Document Receiving Module 320 that is used for receiving electronic documents;
- a Classification/Validation Module 322 that is used for classifying a respective electronic document and validating document information associated with the respective electronic document;
- a Naming Module 324 that is used for naming a respective electronic document;
- an Indexing Module 326 that is used for indexing a respective electronic document;
- an Archiving Module 328 that is used for archiving a respective electronic document;
- a Presentation Module 330 that formats documents and document information for display; and
- Name Schema 338 that includes a list of document types and corresponding document type descriptions; optionally, the name schema 338 may include additional information (e.g., a range of valid folder numbers and cabinet numbers).

In some embodiments, the document receiving module 320 is used for receiving scanned images of physical documents. In some embodiments, the document receiving module 320 is used for receiving electronic documents that are or that include one or more scanned images of physical documents. In some embodiments, the document receiving module 320 receives an electronic document from another computer system (e.g., another client 102 or server) using the network interface 304, from a local storage (e.g., a USB drive, a hard drive, a CD-ROM drive, or other readable medium), and/or from a code reader 104 coupled to the client 102 through the code reader interface 314 (e.g., an image scanner that sends scanned images of a physical document as an electronic document). In some embodiments, the document receiving module 320, the code reader interface 314, or the code reader 104 converts the one or more scanned images of a physical document into an electronic document.

In some embodiments, the document receiving module 320 includes an optical character recognition (OCR) module 332 and/or a code processing module 334. The OCR module 332 is used for identifying characters in scanned images of the physical document. The code processing module 334 is used for identifying and/or decoding machine-readable codes associated with the scanned images of a physical document. Non-limiting examples of machine-readable codes include barcodes, such as linear barcodes (e.g., coded with a plurality of bars, typically of distinct widths), matrix barcodes (also called two-dimensional (2D) barcodes, e.g., a two-dimensional array of patterns), holographic barcodes, codes encoded in RFID signals, and alphanumeric codes. Such machine-readable codes are associated with the electronic document by, for example, printing one or more barcodes on one or more pages of a physical document, attaching one or more labels that include one or more barcodes on one or more pages of the physical document, attaching one or more RFID tags on the physical document, and/or adding a cover page that includes one or more codes (e.g., a cover page that includes barcodes).

In some embodiments, the OCR module 332 and/or the code processing module 334 are included in the code reader interface 314 or in the code reader 104 (e.g., an optical scanner) coupled to the client 102. The OCR module 332 and/or the code processing module 334 are used to extract information stored in the electronic document, in particular, information associated with or stored in the codes in the electronic document. For example, codes (e.g., barcodes) may include a document type ID (e.g., "1130") and a document type description (e.g., "CV" as an abbreviation for curriculum vitae).

In some embodiments, the information extracted from the codes (e.g., barcodes) can be used to retrieve information associated with the codes (e.g., barcodes). For example, if the codes (e.g., one of the barcodes in the electronic document) include a study ID "18113-10," the study ID (which can be or include a category ID, a cabinet ID, a site ID, or any combination thereof) can be used to retrieve related information from the name schema 338 or the local document database 336. Alternatively, the study ID can be used to retrieve related information from the document management server 108 through communication network(s) 106 using the network communication module 312 and the network interface 304.

In some embodiments, the classification/validation module 322 classifies the received electronic document based on the information associated with or stored in the one or more codes (e.g., barcodes). For example, if the barcode of an electronic document includes a study ID "18113-10," where the study ID is a combination of a cabinet number and a folder number, the electronic document is classified as belonging to a cabinet numbered 18113, and a folder numbered 10. In some embodiments, the classification/validation module 332 classifies the received electronic document based on a category ID, which may be a part of a document ID or may be retrieved using information stored in the codes.

In some embodiments, the classification/validation module 322 validates the received electronic document based on the information associated with or stored in the one or more codes (e.g., barcodes). The document type ID (e.g., "1130") is used to locate a corresponding document type description in the name schema 338, and the corresponding document type description in the name schema 338 is compared against the document type description extracted from the codes (e.g., barcodes). If there is a match, the electronic document is deemed to be validated. If there is a mismatch (e.g., due to a scanning error, poor image quality, scanning of an incorrect document, attachment of an incorrect code, etc.), the electronic document may be rejected or an alert is provided, and in addition, a new scan of the physical document can be performed using the code reader interface 314. Additionally, or alternatively, the information associated with or stored in the codes may include a cabinet number and a folder number. The cabinet number and the folder number can also be used to validate the electronic document (e.g., whether the cabinet number and/or the folder number match cabinet numbers and folder numbers in the document database 130 and/or the local document database 336).

In some embodiments, the naming module 324 names the received electronic document based on the information associated with or stored in the codes. For example, if the information associated with or stored in the codes includes: a cabinet number (e.g., 18113), a folder number (e.g., 10), a document type number (e.g., 1130), and a document type description (e.g., "CV"), and if the naming schema (e.g., stored in the name schema 338) is [cabinet number]-[folder number]-[document type number]-[document type description], the electronic document is named such that the name of the electronic document includes a character string "18113-10-1130-CV." The document name may also include a sequential number. For example, if there are two CV documents in the 18113-10 cabinet/folder, the first electronic document can be named as "18113-10-1130-CV-0001" and the second electronic document can be named as "18113-10-1130-CV-0002."

In some embodiments, the indexing module 326 stores document information in the electronic document as metadata. For example, the indexing module 326 stores in the electronic document information stored in the codes as metadata (e.g., after extracting the cabinet number and the folder number from the barcode, the cabinet number and the folder number are stored in the electronic document as metadata). In some embodiments, the information stored in the codes is used to retrieve information associated with the codes (e.g., principal investigator name, clinical trial site name, clinical trial start date, etc.). In some embodiments, the retrieved information associated with the codes is stored in the electronic document as metadata.

In some embodiments, the archiving module 328 archives the electronic document. In some embodiments, archiving the electronic document includes moving the electronic document from the document queue database 132 to the document database 130. In some embodiments, archiving the electronic document includes moving the electronic document from the local document database 336 to the document database 130. In some embodiments, archiving the electronic document includes moving the electronic document from the document database 130 to a remote backup server (not shown).

In some embodiments, one or more of: the document receiving module 320, the classification/validation module 322, the naming module 324, the indexing module 326, and the archiving module 328 are operated automatically (e.g., without human intervention or operation). For example, when a scanned image of a physical document is sent to the client 102 from a code reader 104 coupled to the client 102, the electronic document is validated, named, indexed, and archived without human involvement.

In some embodiments, the presentation module 330 includes a document viewer (e.g., a document image viewer) and a document data viewer (e.g., also called herein a document metadata viewer). The document viewer is configured to format documents (or content of documents) for display, and the document data viewer is configured to format document information (or metadata) for display.

In some embodiments, programs embedded within the web app 116 format documents and document information for display. In some embodiments, the client 102 displays data received from the document management server 108 based on conventional means for exchanging data, without using webpages. For example, a client 102 can display documents and document information received from the document management server 108 without using webpages. In some embodiments, the client 102 receives the documents and document information based on conventional means (e.g., as a non-webpage electronic document, such as a portable document format (PDF) file, or an image file (e.g., a TIFF or JPEG)) and displays at least a portion of the documents and document information as a webpage in the web browser 318. In other embodiments, a client 112 receives documents and document information as webpages, and displays the received webpages using the web browser 318.

As illustrated, the client 102 is a "thin client," which includes a web browser 318 that executes the web app 116, and the client 102 does not need, nor does it use, a locally installed software application. In other embodiments, the client 102 includes a document management application (not shown) that performs functions analogous to the functions of the web app 116 as an independent application (i.e., operates without the web browser 318). In some cases, the client 102 includes both a web app and a separate application, each of which performs one or more functions or analogous functions of the web app 116 described herein.

Figure 4A:
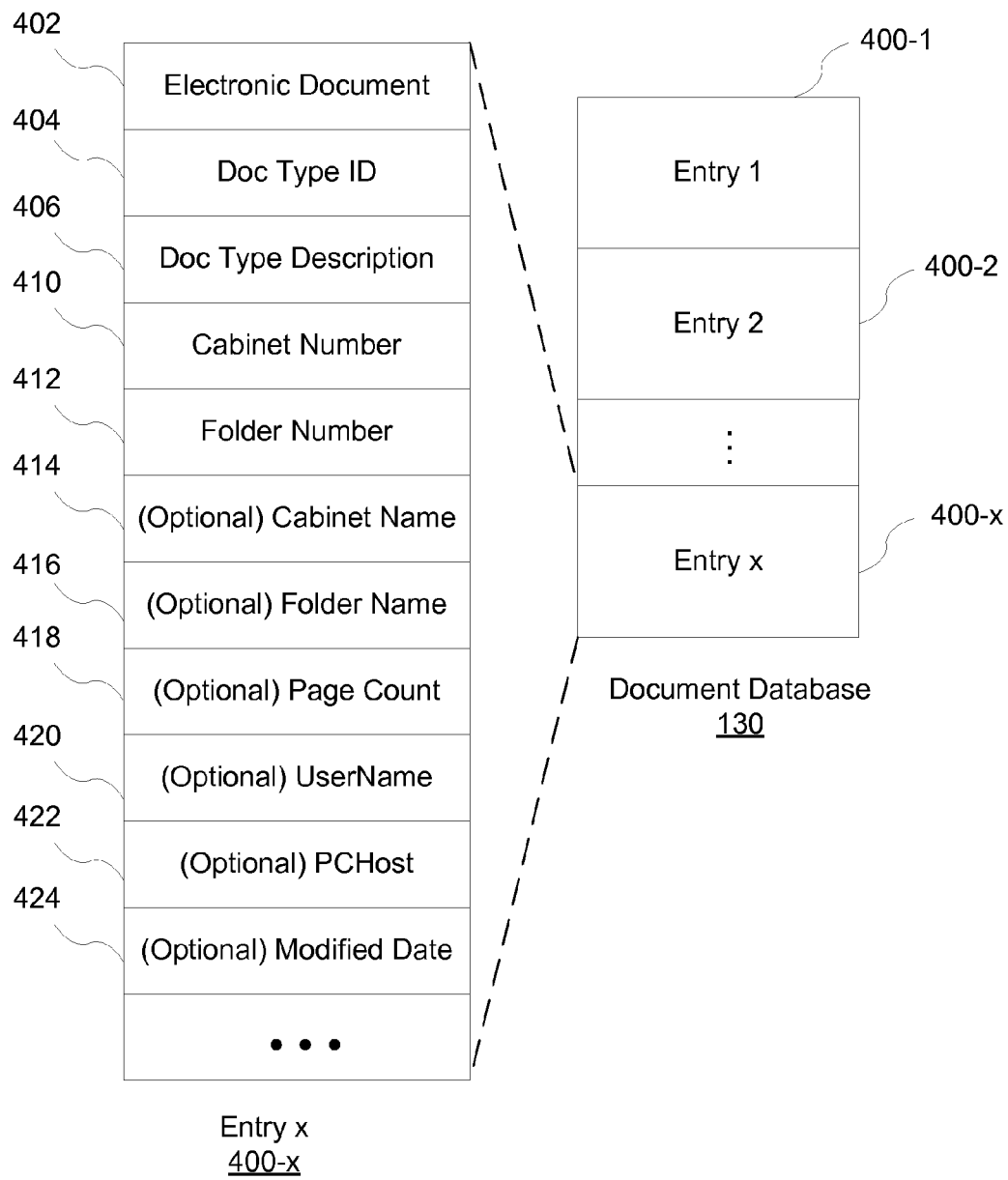
FIG. 4A is a block diagram illustrating an exemplary document database and an exemplary document data entry in the document database in accordance with some embodiments.

FIG. 4A is a block diagram illustrating an exemplary document database and an exemplary document data entry in the document database (e.g., 130) in accordance with some embodiments. The document database 130 stores document data entries, for example document data entry 400-1 through document data entry 400-x, where x may represent the number of document data entries. An entry 400 includes information for a respective electronic document that is waiting for a review and/or edit by a user.

A document data entry (e.g., entry 400-x) includes the following data, or a subset or superset thereof:
  an Electronic Document 402 (e.g., a PDF file containing scanned images of a physical document) or a pointer to the electronic document 402;
  (optional) an Archive Number and Archive Name (not shown) that indicates an archive where the electronic document 402 is archived;
  (optional) a role ID (not shown) that indicates a role for the electronic document 402;
  a Document Version (not shown) that indicates a version of the electronic document 402, which may indicate the revision number of the electronic document 402 or a number of the same type of documents in a given pair of cabinet and folder;
  a Document Type ID 404 that identifies a type of the electronic document 402 (e.g., "1110" for FDA FORM 1572, "1130" for curriculum vitae, etc.);
  a Document Type Description 406 that describes a document type of the electronic document 402 (e.g., 1572" or "FDA FORM 1572", "CV" or "CURRICULUM VITAE", etc.);
  a Cabinet Number 410 and a Folder Number 412, which together classify the electronic document 402 and/or identify a physical location of the physical document corresponding to the electronic document 402;
  a Category ID (not shown) that identifies a category of the electronic document 402;
  (optional) a Cabinet Name 414 and a Folder Name 416, which include description (or descriptive name) corresponding to the cabinet number 410 and the folder number 412, respectively;
  (optional) a Page Count 418 that indicates the number of pages in the electronic document 402;
  (optional) UserName 420, which indicates a user who created (e.g., by scanning a physical document) or last modified the electronic document 402;
  (optional) PCHost 422, which indicates a name of a computer that was used to create or last modify the electronic document 402;
  (optional) Created Date (not shown), which indicates the date (and time) when the electronic document 402 was created;
  (optional) Modified Date 424, which indicates the date (and time) when the electronic document 402 was last modified; and
  (optional) History (not shown) that includes a history of actions taken on the electronic document 402 (e.g., deleting a page, inserting a page, moving a page, etc.).

In some embodiments, the category of the electronic document 402 includes one or more levels of sub-categories. The highest category (also called a primary category) In some embodiments, the Document Type ID 404 includes the category ID (e.g., the first two digits of the document type ID 404 can be a highest level category ID for the electronic document 402). In some embodiments, the next two digits of the document type ID 404 can be a sub-category ID. Non-limiting examples of primary categories include trial management documents, country core documents (for international applications or for international clinical trials), data service documents, and investigator documents, each of which is assigned to a unique category ID.

In some embodiments, the document data entry (e.g., entry 400-x) also includes one or more of: staff name, staff role, date of signature, associate name (e.g., clinical research associate or CRA), and status (e.g., scanned, indexed, archived, etc.). In some embodiments, the document data entry (e.g., entry 400-x) also includes a signature status, which indicates whether the document has been signed, and/or a signer identity, which indicates a person who signed the document (e.g., by name, username, employee number, etc.).

In some embodiments, some of the data in the document data entry 400 are stored in pairs. For example, the cabinet number 410 and the folder number 412 can be stored together as a pair. Similarly, the document type ID 404 and the document type description 406 can be stored together as a pair.

In some embodiments, the fields in the document data entry 400 are filled out by using information stored in the electronic document 402. For example, the cabinet number 410 can be retrieved from the document data entry 400 and stored in the electronic document 402. In some embodiments, at least some of the fields in the document data entry 400 are filled out by using information retrieved using one or more pieces of information stored in the electronic document 402 (e.g., the folder number 412 and the cabinet number 410 can be used to extract other information, such as the folder name and the cabinet name, from the name schema 338, the local document database 336, and/or the document database 130). In some embodiments, the data in the document data entry 400 are stored in the electronic document 402 as metadata. For example, the cabinet name 414 can be retrieved from the document database 130 and stored in the electronic document 402.

In some embodiments, the document queue database 132 has a similar structure as the document database 130 as illustrated in FIG. 4A.

Figure 4B:
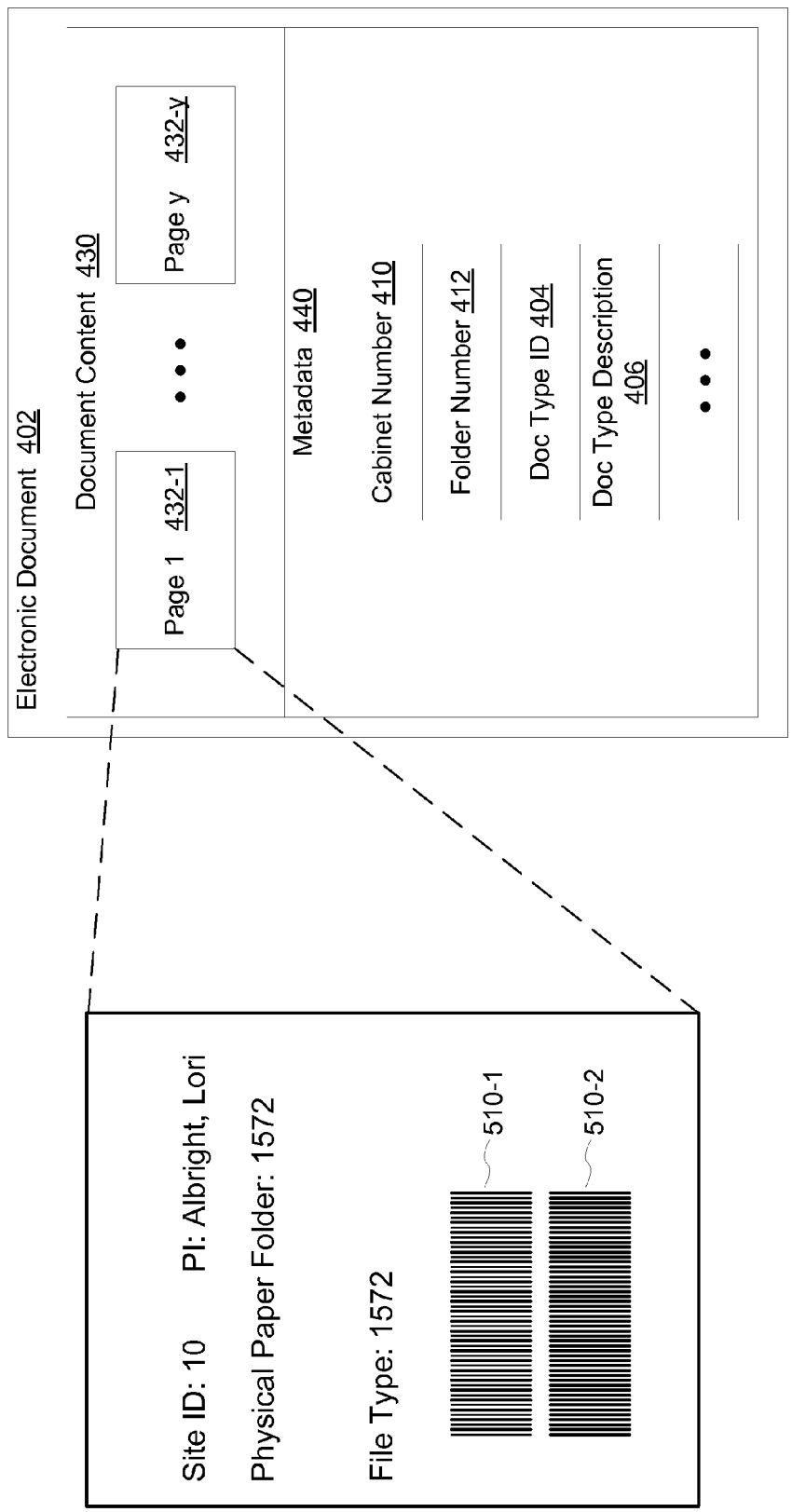
FIG. 4B is a block diagram illustrating a data structure of an exemplary electronic document in accordance with some embodiments.

FIG. 4B is a block diagram illustrating a data structure of an exemplary electronic document in accordance with some embodiments.

The electronic document 402 includes document content 430 and metadata 440. The metadata 440 refers to data about the document content 430 (e.g., data providing information about creation, revision, and access of the document content 430 and/or the nature and status of the document content 430). In some embodiments, the metadata 430 is not included in the document content 430. For example, although author information, document creation date, and document revision history can be included in the document content 430 (e.g., the document may list such information on its one or more pages), such information included in the document content 430 is not metadata. Typically, the metadata 440 is stored in a portion of the electronic document 402 that is not configured to be viewed by a document content viewer/editor. The metadata 440 can be accessed with a document metadata viewer or a document metadata viewing command. In some embodiments, the metadata 440 includes document information described with reference to FIG. 4A (e.g., the cabinet number 410, the folder number 412, the document type ID 404, the document type description 406, etc.). The metadata 440 can be included in the electronic document 402 as a single set of data (e.g., all metadata is stored in one portion of the electronic document 402), or in a plurality of portions in the electronic document 404. For example, a PDF file includes a document information dictionary, which includes author, title, subject, creation and update date information; and metadata streams, which are metadata based on Extensible Markup Language (XML) specifications, added using the Extensible Metadata Platform (XMP™) standard.

Document content 430 includes scanned images of a physical document. As illustrated, a respective scanned image may correspond to each page of the physical document (e.g., page 1 (432-1) through page y (432-y)), although a single scanned image may correspond to a portion of a page or multiple pages of a physical document. In some embodiments, at least one image (e.g., the first image (page 1 432-1) or the last image (page y 432-y)) of the physical document includes one or more barcodes (e.g., 510-1 and 510-2) and additional document information that can be read by users (e.g., site ID, principal investigator (PI) name, file type, etc.). Such barcodes and additional document information are stored as images, and therefore can be extracted only by using the OCR module 332 and/or the code processing module 334 (shown in FIG. 3). In some embodiments, after the codes and additional document information are extracted by the OCR module 332 and/or the code processing module 334, at least one scanned image that includes one or more barcodes is deleted or removed from the scanned images of the physical document.

In some embodiments, in order to make the first scanned image of a physical document include one or more barcodes, a coversheet including one or more barcodes (as illustrated in FIG. 4B as page 1 432-1) is added to each regulatory document prior to scanning the physical document. However, the first scanned image of the physical document may be deleted after document information associated with the one or more barcodes is stored in the electronic document.

Figure 5A:
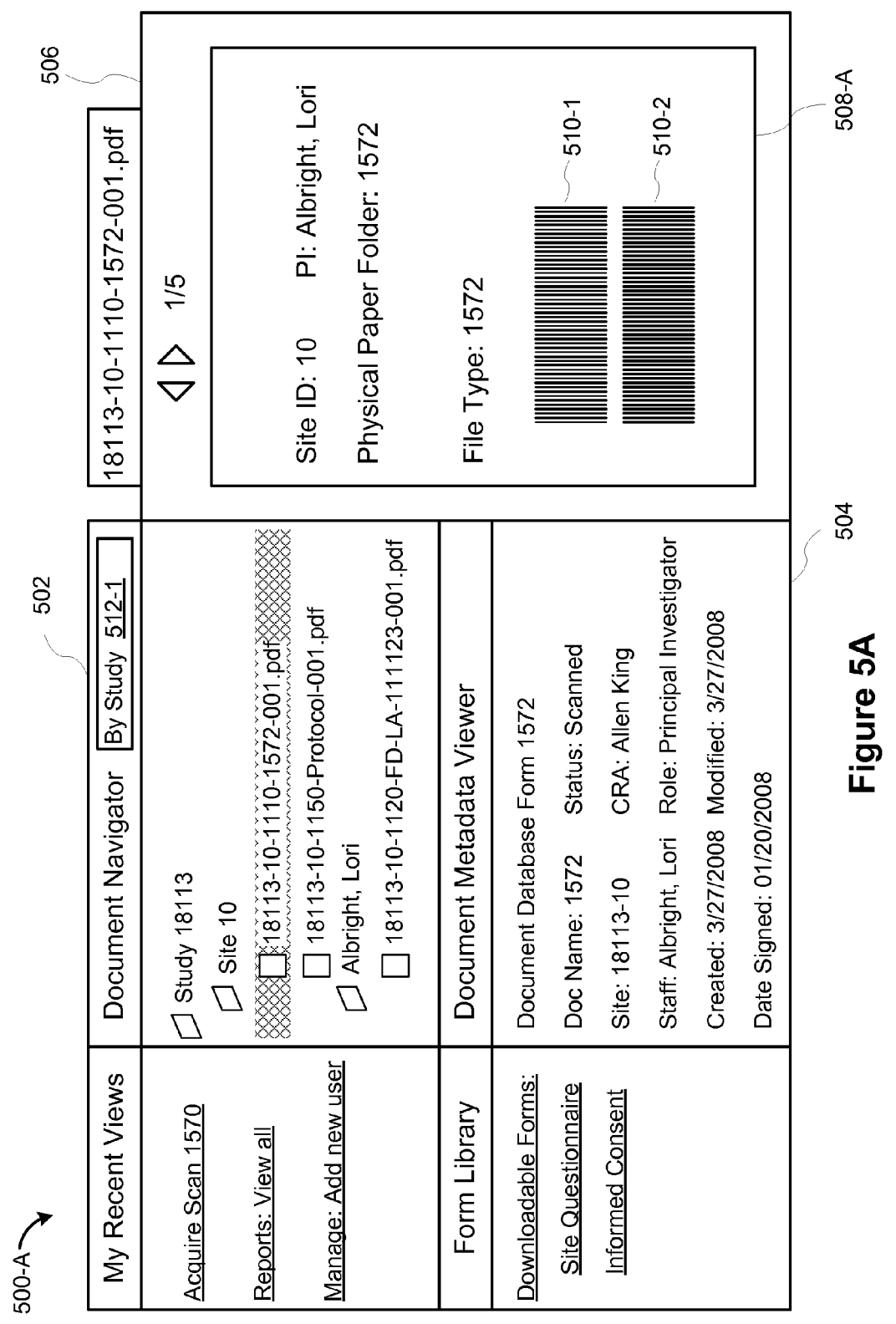

FIGS. 5A-5B are exemplary user interfaces of a web application 116 displayed on a GUI 111 of a client 102 in accordance with some embodiments.

FIG. 5A illustrates an exemplary user interface 500-A displaying document information metadata and a scanned image of a physical document in accordance with some embodiments. The user interface 500-A includes a document navigator 502, which allows a user to view and select a cabinet, folder, and document in a plurality of clinical trial documents. In some embodiments, cabinets, folders, and documents are typically organized hierarchically (e.g., in a tree structure) in the document navigator 502. In some embodiments, the document navigator 502 includes a pull-down menu to select a type of data (e.g., 512-1), and the hierarchy of documents is rearranged in accordance with the selected data type (e.g., study, site, category, staff, contact, etc.). For example, when a user selects to rearrange the hierarchy of documents in accordance with study (as shown in FIG. 5A), all folders and documents are arranged for respective studies. In FIG. 5A, the "study 18113" cabinet includes two bins: the "site 10" bin and "the Albright, Lori" bin. The "site 10" bin contains two documents, entitled "18113-10-1110-1572-001.pdf" and "18113-10-1150-Protocol-001.pdf." In this example, the "18113-10-1110-1572-001.pdf" document is selected, and corresponding document information and document content are displayed in the user interface 500-A.

The document metadata viewer 504 displayed in the user interface 500-A includes document information stored in the selected document "18113-10-1110-1572-001.pdf" as metadata. In some embodiments, the document metadata viewer 504 extracts and displays the document information in the selected document "18113-10-1110-1572-001.pdf" as metadata when the document "18113-10-1110-1572-001.pdf" is selected. In some embodiments, the document metadata viewer 504 creates a database index (and stores in the local document database 336) or receives, and retrieves from, the database index any document information to be displayed in the user interface 500-A. The displayed metadata include: document name, site ID, staff name, created date, modified date, date of signature, etc.

The document image viewer 506 displayed in the user interface 500-A includes a scanned image 508-A of a physical document. In some embodiments, as illustrated, the first image of the physical document comprises an image of a barcode coversheet that includes a plurality of barcodes (e.g., 510-1 and 510-2). However, in some embodiments, the barcode coversheet is deleted from the scanned images of the physical document, and thus, the first image of the physical document may not include an image of one or more barcodes. The document image viewer 506 also indicates that the displayed image is a first image out of total of five images (as indicated by the text "1/5"). The document image viewer also includes a plurality of user interface objects, including navigation buttons (illustrated as left and right-facing triangles) which allow a user to navigate to previous and next images, respectively.

In FIG. 5B, the exemplary user interface 500-B is similar to the user interface 500-A shown in FIG. 5A, except that the document image viewer shows a second scanned image 508-B of the physical document. As illustrated, the metadata in the document metadata viewer 504 and the scanned image of the document in the document image viewer 506 are concurrently displayed on the user interface 500-B. Such concurrent display greatly facilitates a user to find and interpret regulatory documents, as the metadata provides additional information in understanding the regulatory documents.

Figure 6A:
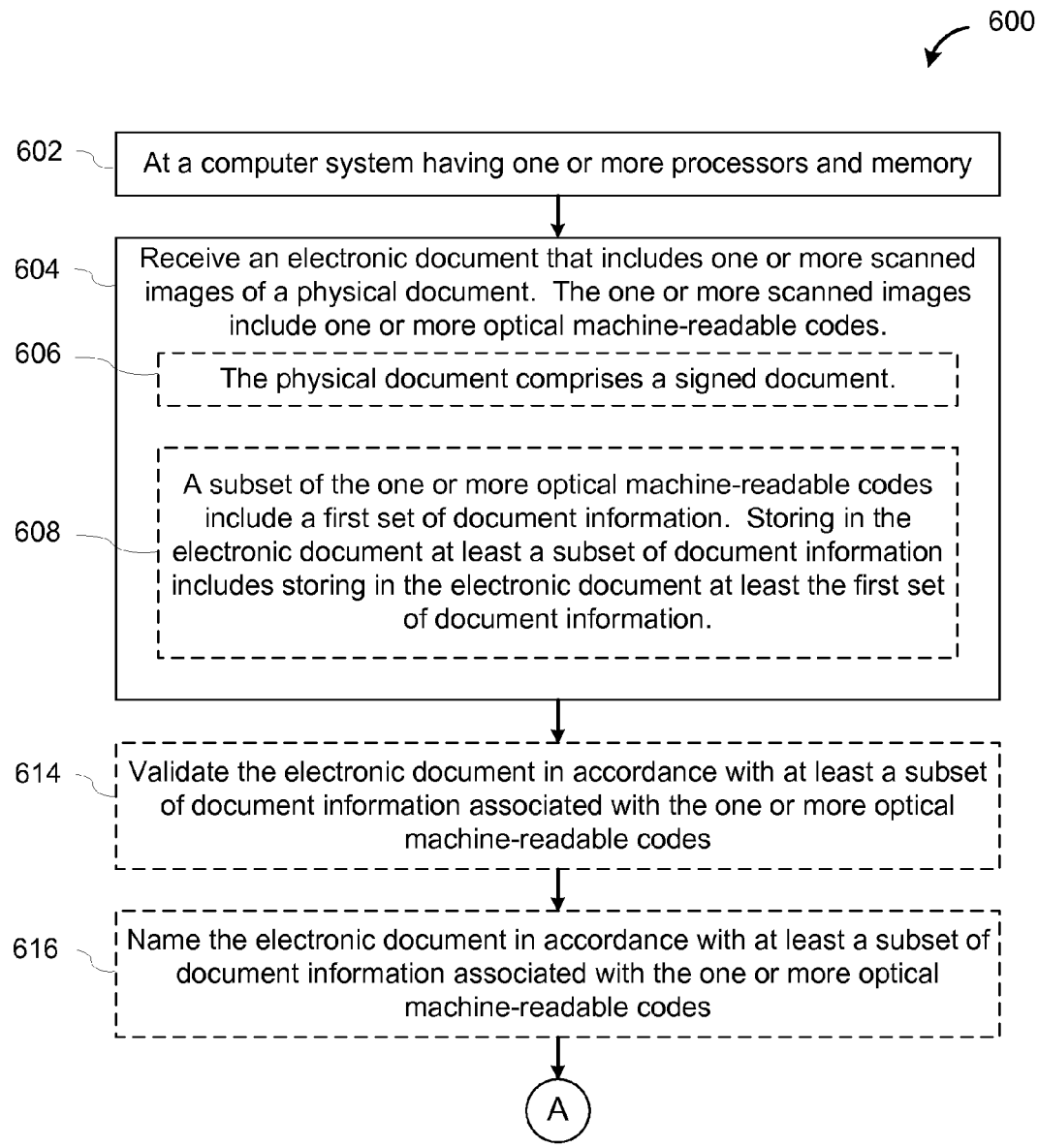
FIGS. 6A-6C are flowcharts representing a method of storing document information as metadata in an electronic document in accordance with some embodiments.
Figure 6B:
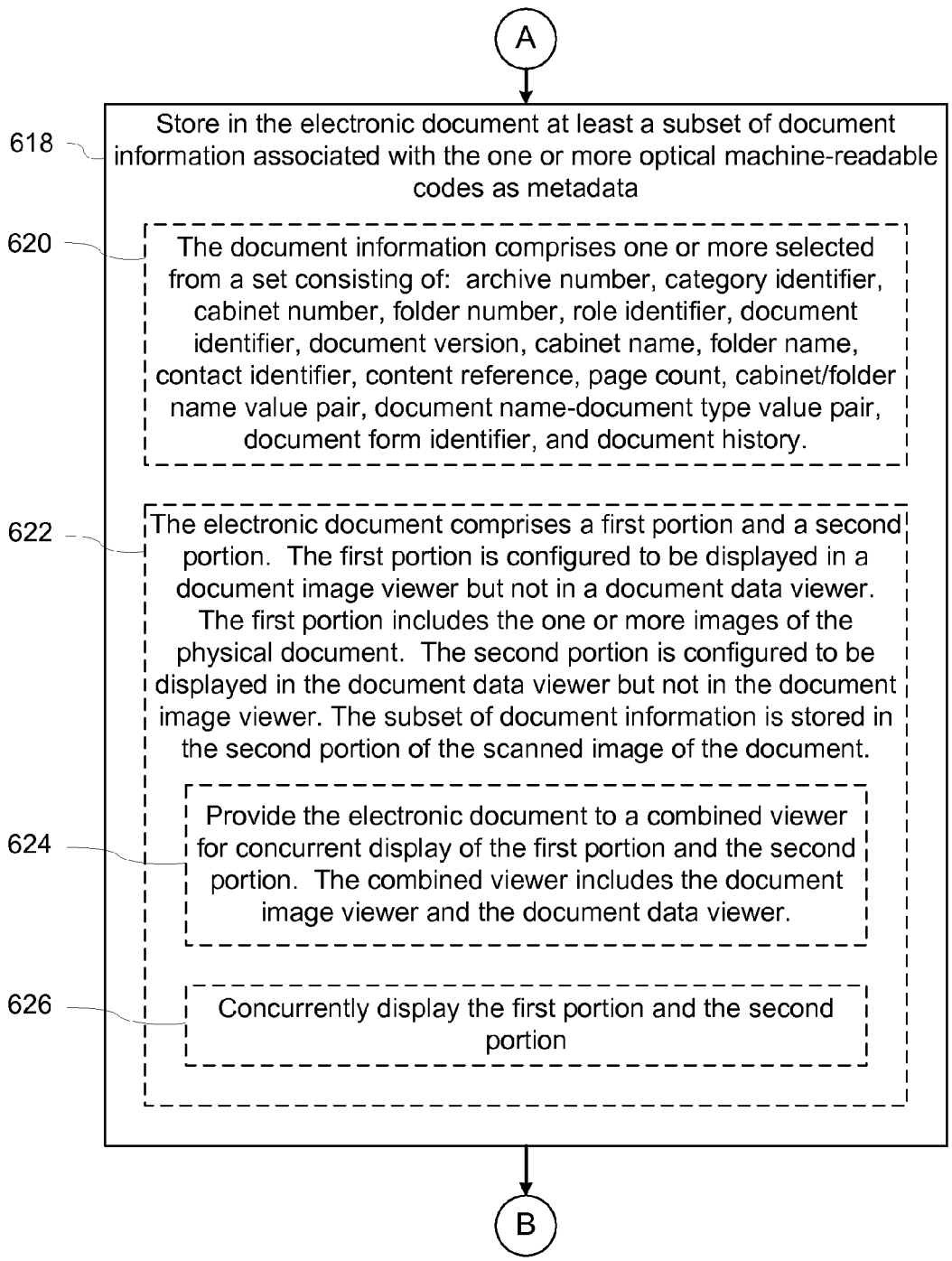
Figure 6C:
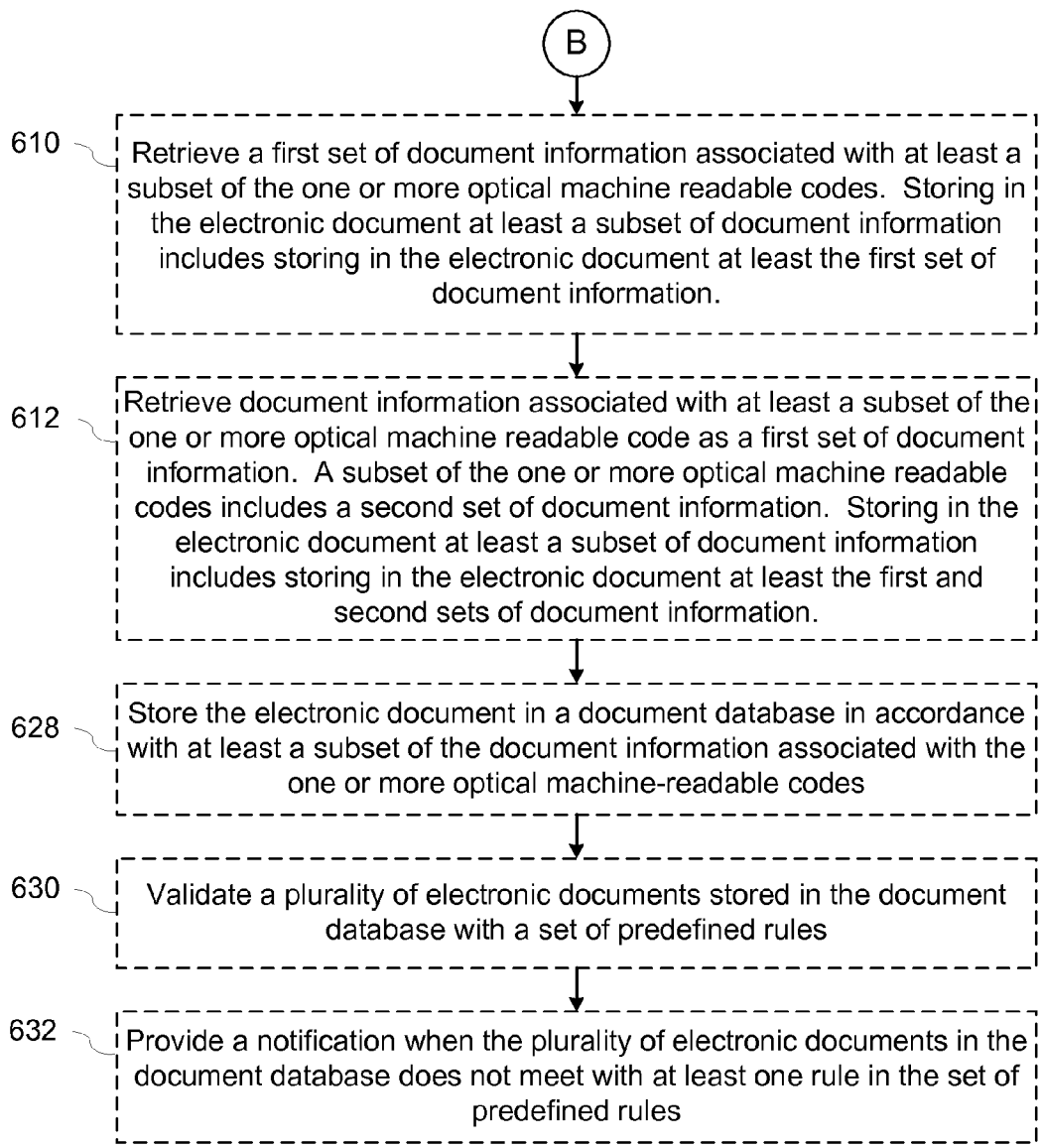

FIGS. 6A-6C are flowcharts representing a method 600 of storing document information as metadata in an electronic document in accordance with some embodiments. The computer-implemented method 600 is performed (602) at a computer system (e.g., the client 102 or the distributed computer system 100) having one or more processors and memory storing one or more programs for execution by the one or more processors to perform the method.

The computer system receives (604) an electronic document that includes one or more scanned images of a physical document (e.g., Pages 432-1 through 432-y in FIG. 4B are scanned images of a physical document). The one or more scanned images include one or more optical machine-readable codes (e.g., barcodes 510-1 and 510-2 in FIG. 4B).

In some embodiments, the physical document comprises (606) a signed document. In some embodiments, the signed document is or includes a "wet" signed document (e.g., signed in ink on paper). In some embodiments, the signed document is or includes a digitally signed document. In some embodiments, the document comprises a clinical trial document.

In some embodiments, a subset of the one or more optical machine-readable codes includes (608) a first set of document information. Storing in the electronic document at least a subset of document information includes storing in the electronic document at least the first set of document information. For example, the barcodes 510-1 and 510-2 in FIG. 4B may include a cabinet number, a folder number, a document type ID, and a document type description. Such information can be extracted from the barcodes 510-1 and 510-2 using the code processing module 334, and stored in the electronic document. In some embodiments, a subset of the first set of document information is stored in the electronic document (e.g., not all document information extracted from the barcode is stored in the electronic document).

In some embodiments, the computer system validates (614) the electronic document in accordance with at least a subset of document information associated with the one or more optical machine-readable codes. For example, the computer system uses the classification/validation module 322 to identify a document name description corresponding to a document name type ID from the name schema 338, the local document database 336, and/or the document database 130, and compares the corresponding document name description with the document name description extracted from the barcodes. If there is a match, the electronic document is deemed to be validated. Similarly, any other information in the barcodes can be used to validate the electronic document by checking the range or bounds of values and/or by checking whether the document information stored in the barcodes matches reference information (stored in the name schema 338, the local document database 336, and/or the document database 130).

In some embodiments, the computer system names (616) the electronic document in accordance with at least a subset of document information associated with the one or more optical machine-readable codes. In some embodiments, the computer system uses a predefined naming rule stored in the name schema 338, the local document database 336, the document database 130, and/or the web app 116. For example, the computer system can name an electronic document as "[cabinet number]-[folder number]-[document type ID]-[document type description]-[document version].[file type]."

The computer system stores (618) in the electronic document at least a subset of document information associated with the one or more optical machine-readable codes as metadata. For example, when the code (e.g., barcode) information includes the cabinet number and the folder number, the computer system stores the cabinet number and the folder number as metadata in the electronic document. Storing document information as metadata is different from storing the document information as part of the document content because information in the document content can be viewed by a document viewer. The metadata is not intended to be viewed as part of the document content. Instead, the metadata is configured to provide additional information, which can be used to index the electronic document and/or to provide context in understanding the document content.

In some embodiments, the document information comprises (620) one or more selected from a set consisting of: archive number, category identifier, cabinet number, folder number, role identifier, document identifier, document version, archive name, cabinet name, folder name, contact identifier, content reference, page count, cabinet/folder name value pair, document name-document type value pair, document form identifier, and document history. In some embodiments, the cabinet/folder name value pair is or includes a single data entry that includes both the cabinet name and the folder name (e.g., in a format such as [cabinet name]-[folder name]). In some embodiments, the document name-document type value pair is or includes a single data entry that includes both the document name and the document type value (e.g., in a format such as [document type value]-[document name]). In some embodiments, the document information also includes creation date, modification date, user name, and the name of a computer system that was used to create or modify the document.

In some embodiments, the electronic document comprises (622) a first portion and a second portion. The first portion is configured to be displayed in a document image viewer but not in a document data viewer. The first portion includes the one or more images of the physical document (e.g., in FIG. 4B, the document content 430 of the electronic document 402 includes one or more images of a physical document). In some embodiments, the document image viewer is configured to display scanned images of documents (e.g., the document image viewer 506 is configured to display a scanned image 508-A of the document). In some embodiments, the document data viewer is configured to display metadata of scanned images of documents (e.g., the document metadata viewer 504 is configured to display metadata of scanned images). The second portion is configured to be displayed in the document data viewer but not in the document image viewer (e.g., the metadata is not configured to be displayed in the document image viewer 506). The document information is stored in the second portion of the scanned image of the document.

In some embodiments, the computer system provides (624) the electronic document to a combined viewer for concurrent display of the first portion and the second portion. The combined viewer includes the document image viewer and the document data viewer (e.g., the web app 116 includes the document image viewer and the document data viewer, and the user interface 500 of the web app 116 includes the document image viewer 506 and the document data viewer 504 in FIG. 5A). In some embodiments, such combined viewer is implemented as the presentation module 330 (FIG. 3). In other embodiments, the combined viewer is implemented in the web app 116, the web browser 318, or any other application in the applications 316.

In some embodiments, the computer system concurrently displays (626) the first portion and the second portion (e.g., in FIG. 5A, the scanned image 508-A and the metadata are concurrently displayed).

In some embodiments, the computer system retrieves (610) a first set of document information associated with at least a subset of the one or more optical machine readable codes. Storing in the electronic document at least a subset of document information includes storing in the electronic document at least the first set of document information. For example, the computer system first extracts information from the barcodes (e.g., the cabinet number and the folder number), and using the information extracted from the barcode, retrieves additional information from the name schema 338, the local document database 336, and/or the document database 130 (e.g., the cabinet name, the folder name, and/or the principal investigator name). In other embodiments, the machine readable codes contain such additional information.

In some embodiments, the computer system retrieves (612) document information associated with at least a subset of the one or more optical machine readable code as a first set of document information. A subset of the one or more optical machine readable codes (e.g., one or more of the optical machine readable codes) includes a second set of document information. Storing in the electronic document at least a subset of document information includes storing in the electronic document at least the first and second sets of document information. For example, the computer system extracts the cabinet number and the folder number from barcodes, and retrieves additional information (e.g., the cabinet name and the folder name) using the cabinet number and the folder number. Then the computer system stores the cabinet number, folder number, cabinet name, and folder name in the electronic document.

In some embodiments, the computer system stores (628) the electronic document in a document database in accordance with at least a subset of the document information associated with the one or more optical machine-readable codes (e.g., the computer system stores the electronic document in the document database 130 in accordance with the cabinet number and the folder number extracted from barcodes). In some embodiments, the computer system creates an index of electronic documents stored in the document database 130. In some embodiments, the computer system identifies an electronic document using the index of electronic documents, and retrieves the identified electronic document. In some embodiments, the computer system creates a hierarchy of documents stored in the document database 130.

In some embodiments, the computer system validates (630) a plurality of electronic documents stored in the document database with a set of predefined rules. In some embodiments, the set of predefined rules includes identifying one or more missing electronic documents in accordance with the set of predefined rules. In some embodiments, the computer system retrieves a set of study rules (stored in the document database 130 or separately in the web app server 114). For example, the set of study rules may require an "informed consent" document to be signed by each patient. If a study (e.g., documents stored in a particular set of cabinets and folders) includes informed consent documents for all participating patients, and if all informed consents documents are signed (e.g., based on signature dates), the plurality of electronic documents are deemed to be validated.

In some embodiments, the computer system provides (632) a notification when the plurality of electronic documents in the document database does not meet with at least one rule in the set of predefined rules. The computer system may provide the notification using a visual indication (e.g., signs, symbols, popup boxes, etc.), or a message (e.g., an email notification, a text message, etc.) to one or more recipients based on their roles (e.g., send to all principal investigators associated with the study).

In some embodiments, the scanned image is configured in accordance with Portable Document Format. In some embodiments, the metadata is stored in an Extensible Metadata Platform format.

Note that details of the processes described above with respect to the method 600 are also applicable in an analogous manner to methods 700, 800, and 900 described below. For brevity, these details are not repeated below.

Figure 7:
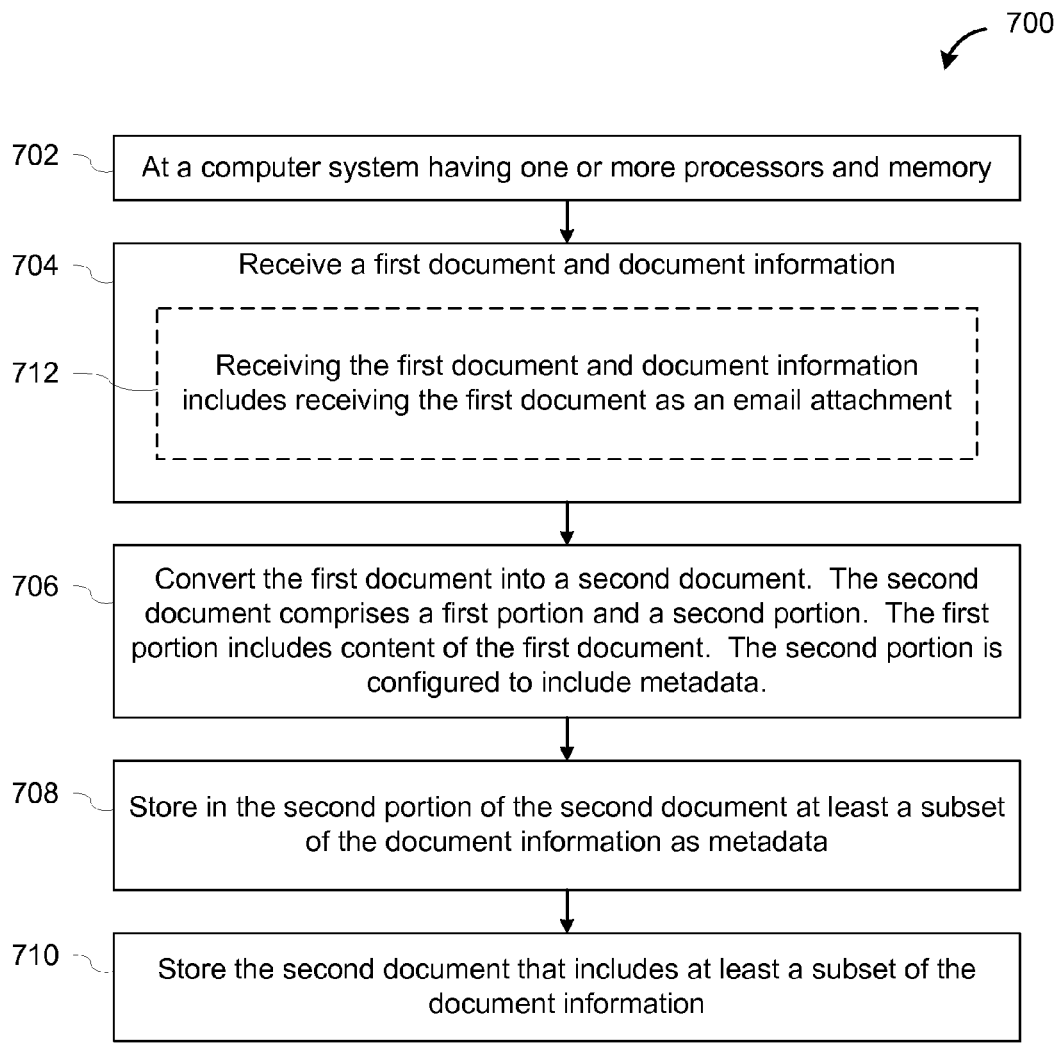
FIG. 7 is a flowchart representing a method of storing document information as metadata in a converted document in accordance with some embodiments.

FIG. 7 is a flowchart representing a method 700 of storing document information as metadata in a converted document in accordance with some embodiments. The computer-implemented method 700 is performed (702) at a server (e.g., 112) having one or more processors and memory storing one or more programs for execution by the one or more processors to perform the method.

The computer system receives (704) a first document and document information. Exemplary document information includes the cabinet number and the folder number, and any other document information discussed with reference to FIG. 4A. In some embodiments, the first document may be an email or a word-processor document as an attachment to an email, received through an email server 224. In such embodiments, the email includes at least a subset of the document information.

In some embodiments, receiving the first document and document information includes (712) receiving the first document as an email attachment (e.g., using the email server 224 in FIG. 2 or an email application software (not shown) in a client 102).

The computer system converts (706) the first document into a second document (e.g., the first document is converted into a PDF file). The second document comprises a first portion and a second portion. The first portion includes content of the first document, and the second portion is configured to include metadata (e.g., the PDF file has one or more portions for document content, and one or more portions for metadata).

The computer system stores (708) in the second portion of the second document at least a subset of the document information as metadata (e.g., at least a subset of the received document information is stored as metadata in the PDF file).

In some embodiments, the computer system retrieves document information associated with at least a subset of the received document information (e.g., the cabinet name based on the cabinet number).

The computer system stores (710) the second document that includes at least a subset of the document information (e.g., in the document database 130, the document queue database 132, or the local document database 336). In some embodiments, the computer system (or the document management server 108 of the computer system) stores the second document in the document database 130. In some embodiments, the computer system sends (e.g., as an email attachment) the stored second document that includes the document information to one or more users such that the electronic document can be used for other purposes (e.g., review, auditing, etc.).

In some embodiments, the computer system receives an email with a plurality of attachments, and at least a subset of the document information. The computer system stores document information in the plurality of attachments. For example, when the computer system receives an email with a cabinet number 018113 and a folder number 10, the same cabinet and folder numbers are stored in all attachments of the email.

Figure 8:
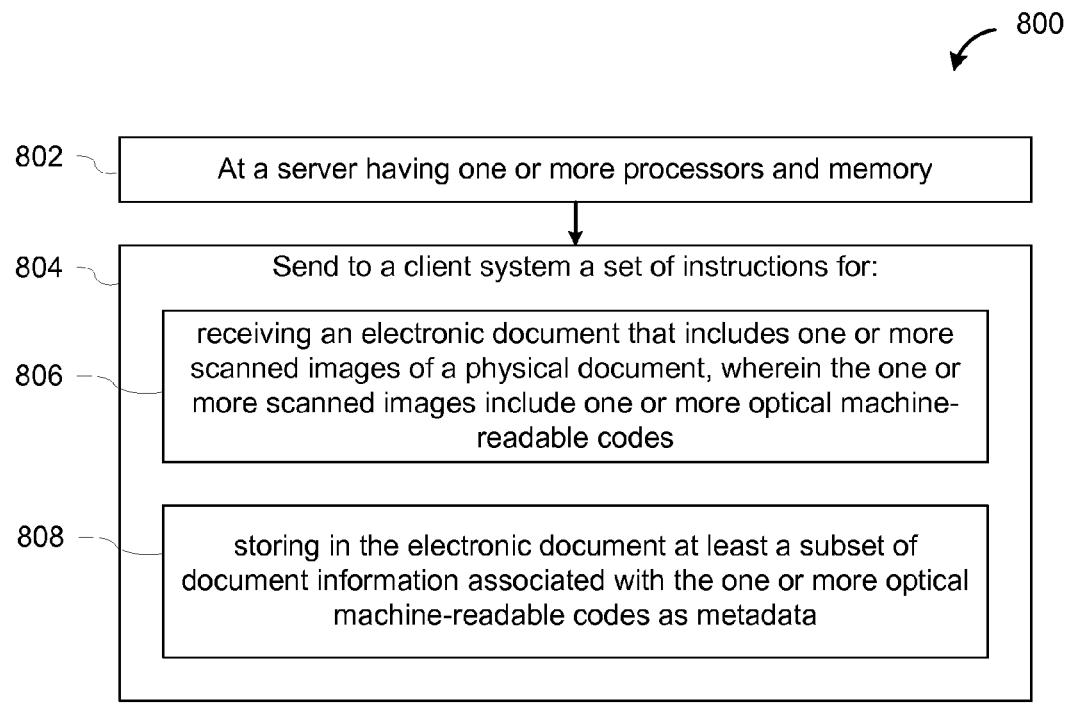
FIG. 8 is a flowchart representing a method of sending to a client system instructions for storing document information in an electronic document in accordance with some embodiments.

FIG. 8 is a flowchart representing a method 800 of sending to a client system instructions for storing document information in an electronic document in accordance with some embodiments. The computer-implemented method is performed (802) at a server (e.g., document management server 108) having one or more processors and memory. The method is performed typically using the web app server 114, in particular the application distribution module 214 (shown in FIG. 2).

The server sends (804) to a client system (e.g., 102) a set of instructions. The set of instructions includes (806) instructions for receiving an electronic document that includes one or more scanned images of a physical document. The one or more scanned images include one or more optical machine-readable codes.

The set of instructions includes (808) instructions for storing in the electronic document at least a subset of document information associated with the one or more optical machine-readable codes as metadata.

Figure 9:
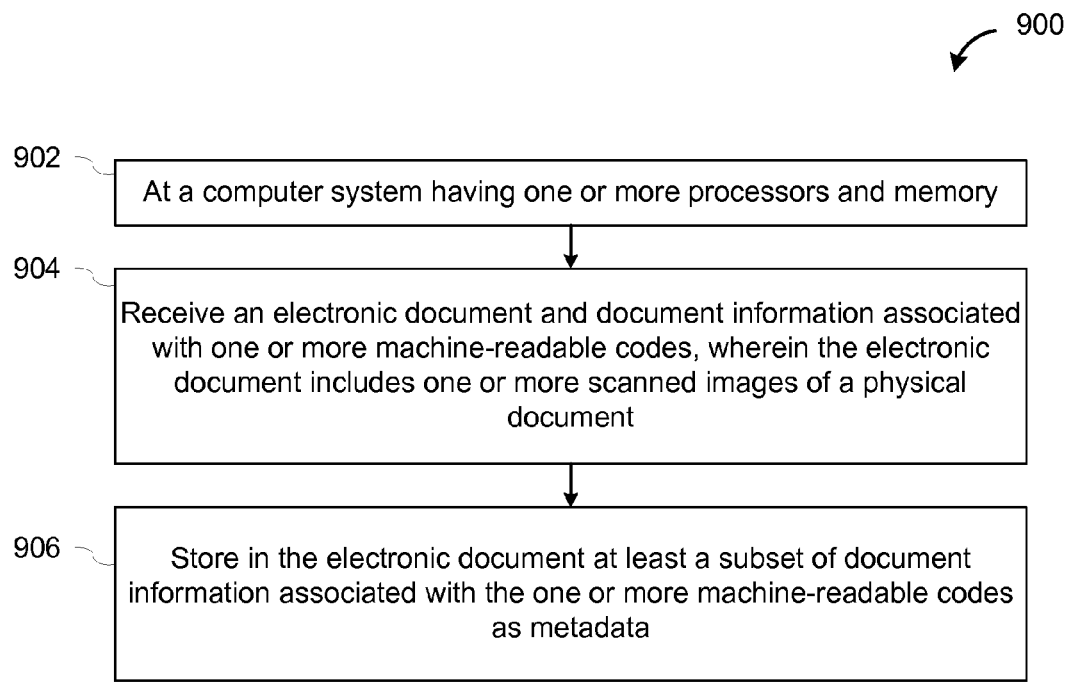
FIG. 9 is a flowchart representing a method of storing document information associated with machine-readable codes in an electronic document as metadata in accordance with some embodiments.

FIG. 9 is a flowchart representing a method 900 of storing document information associated with machine-readable codes in an electronic document as metadata in accordance with some embodiments. The computer-implemented method is performed (902) at a computer system having one or more processors and memory.

The computer system receives (902) an electronic document and document information associated with one or more machine-readable codes (e.g., barcodes, RFID tags, etc.). The electronic document includes one or more scanned images of a physical document. In some embodiments, the document information associated with the one or more machine-readable codes include document information stored in the one or more machine-readable codes (e.g., data stored in one or more barcodes or in RFID signal). In some embodiments, the document information associated with the one or more machine-readable codes include document information retrieved using information stored in the one or more machine-readable codes.

The computer system stores (904) in the electronic document at least a subset of document information associated with the one or more machine-readable codes as metadata.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method, comprising:
   at a computer system having one or more processors and memory:
      receiving an electronic document that includes one or more scanned images of a physical document, wherein the one or more scanned images include one or more optical machine-readable codes;
      extracting a first set of document information from at least a subset of the one or more optical machine readable codes;
      after extracting the first set of document information from at least the subset of the one or more optical machine readable codes, automatically, without human intervention, transmitting a query generated based on the first set of document information to a server requesting a second set of document information, wherein the second set of document information is stored in a pre-existing database by the server;
      in response to the query, retrieving, from the server, the second set of document information, wherein the second set of document information is distinct from the first set of document information;
      storing at least (A) the extracted first set of document information and (B) the retrieved second set of document information as metadata in the electronic document;
      wherein:
         the electronic document comprises a first portion and a second portion;
         the first portion is configured to be displayed in a document image viewer but not in a document data viewer, the first portion including the one or more images of the physical document, wherein a first image of the one or more images corresponds to a page of the physical document and includes at least one of the one or more optical machine-readable codes and at least one of a subset of the first set of document information and a subset of the second set of document information that can be read by users;
         the second portion is configured to be displayed in the document data viewer but not in the document image viewer; and
         the subset of document information is stored in the second portion of the scanned image of the document and
      providing the electronic document to a combined viewer for concurrent display of the first portion and the second portion, wherein the combined viewer includes the document image viewer and the document data viewer.

2. The method of claim 1, wherein the physical document comprises a signed document.

3. The method of claim 1, wherein the document information metadata comprises one or more selected from a set consisting of: archive number, category identifier, cabinet number, folder number, role identifier, document identifier, document version, cabinet name, folder name, contact identifier, content reference, page count, cabinet/folder name value pair, document name-document type value pair, document form identifier, and document history.

4. The method of claim 1, further comprising concurrently displaying the first portion and the second portion.

5. The method of claim 1, further comprising validating the electronic document in accordance with at least one of a subset of the first set of document information and a subset of the second set of document information.

6. The method of claim 1, further comprising naming the electronic document in accordance with at least a subset of document information associated with at least one of a subset of the first set of document information and a subset of the second set of document information.

7. The method of claim 1, further comprising storing the electronic document in a document database in accordance with at least one of a subset of the first set of document information and a subset of the second set of document information.

8. The method of claim 6, further comprising validating a plurality of electronic documents stored in the document database with a set of predefined rules.

9. The method of claim 7, further comprising providing a notification when the plurality of electronic documents in the document database does not meet with at least one rule in the set of predefined rules.

10. A system, comprising one or more processors and memory storing one or more programs when executed by the one or more processors cause the system to:
   receive an electronic document that includes one or more scanned images of a physical document, wherein the one or more scanned images include one or more optical machine-readable codes;
   extract a first set of document information from at least a subset of the one or more optical machine readable codes;
   after extracting the first set of document information from at least the subset of the one or more optical machine readable codes, automatically, without human intervention, transmit a query generated based on the first set of document information to a server requesting a second set of document information, wherein the second set of document information is stored in a pre-existing database by the server;

in response to the query, retrieve, from the server, the second set of document information, wherein the second set of document information is distinct from the first set of document information; and store at least (A) the extracted first set of document information and (B) the retrieved second set of document information as metadata in the electronic document;

wherein:

the electronic document comprises a first portion and a second portion;

the first portion is configured to be displayed in a document image viewer but not in a document data viewer, the first portion including the one or more images of the physical document, wherein a first image of the one or more images corresponds to a page of the physical document and includes at least one of the one or more optical machine-readable codes and at least one of a subset of the first set of document information and a subset of the second set of document information that can be read by users;

the second portion is configured to be displayed in the document data viewer but not in the document image viewer; and the subset of document information is stored in the second portion of the scanned image of the document; and provide the electronic document to a combined viewer for concurrent display of the first portion and the second portion, wherein the combined viewer includes the document image viewer and the document data viewer.

11. A non-transitory computer readable storage medium storing one or more programs for execution by one or more processors in a computer system, the one or more programs including instructions that when executed by the one or more processors cause the electronic device to:

receive an electronic document that includes one or more scanned images of a physical document, wherein the one or more scanned images include one or more optical machine-readable codes;

extract a first set of document information from at least a subset of the one or more optical machine readable codes;

after the extracting the first set of document information from at least the subset of the one or more optical machine readable codes, automatically, without human intervention, transmit a query generated based on the first set of document information to a server requesting a second set of document information, wherein the second set of document information is stored in a pre-existing database by the server;

in response to the query, retrieve, from the server, the second set of document information, wherein the second set of document information is distinct from the first set of document information; and store at least (A) the extracted first set of document information and (B) the retrieved second set of document information as metadata in the electronic document;

wherein:

the electronic document comprises a first portion and a second portion;

the first portion is configured to be displayed in a document image viewer but not in a document data viewer, the first portion including the one or more images of the physical document, wherein a first image of the one or more images corresponds to a page of the physical document and includes at least one of the one or more optical machine-readable codes and at least one of a subset of the first set of document information and a subset of the second set of document information that can be read by users;

the second portion is configured to be displayed in the document data viewer but not in the document image viewer; and the subset of document information is stored in the second portion of the scanned image of the document; and provide the electronic document to a combined viewer for concurrent display of the first portion and the second portion, wherein the combined viewer includes the document image viewer and the document data viewer.

12. The method of claim 1, further comprising:

prior to providing the electronic document to the combined viewer, removing at least one scanned image from the one or more scanned images of the physical document, wherein the at least one scanned image includes a plurality of optical machine-readable codes.

* * * * *